United States Patent

Sounik et al.

[11] Patent Number: 5,493,062
[45] Date of Patent: Feb. 20, 1996

[54] PROCESS FOR PREPARING 4-HYDROXYSTYRENE

[75] Inventors: James R. Sounik, Corpus Christi; William W. Wilkison, III, Richardson; Keith M. Russ, Corpus Christi, all of Tex.

[73] Assignee: Hoechst Celanese Corporation, Somerville, N.J.

[21] Appl. No.: 359,224

[22] Filed: Dec. 19, 1994

[51] Int. Cl.$^6$ .................................................. C07C 39/06
[52] U.S. Cl. ........................ 568/780; 568/716; 568/763
[58] Field of Search ............................. 568/716, 780, 568/715, 781

[56] References Cited

U.S. PATENT DOCUMENTS 4,032,513  6/1977  Fujiwara et al. .
5,087,772  2/1992  Sheehan et al. ........................ 568/804
5,241,098  8/1993  Kvakovszky et al. .................. 558/270
5,274,174  12/1993  Shah et al. ............................ 560/130

Primary Examiner—Werren B. Lone
Attorney, Agent, or Firm—James J. Mullen; Donald R. Cassady

[57] ABSTRACT

The present invention provides a unique and novel way of producing vinyl phenols such as p-vinyl phenol (4-hydroxystyrene—HSM). In this new process, p-α-aminoethylphenol (AEP) is heated under suitable deamination conditions of temperature and pressure and for a sufficient period of time to form the 4-hydroxystyrene (HSM).

9 Claims, No Drawings

5,493,062

PROCESS FOR PREPARING 4-HYDROXYSTYRENE

BACKGROUND OF THE INVENTION

1. Field of the Invention

The present invention relates to a process for the production of 4-hydroxystyrene (HSM), also known as paravinylphenol or p-vinyl phenol, by the deamination of p-α-amino- ethylphenol (AEP) ("α" means alpha herein).

2. Description of the Prior Art

4-Hydroxystyrene (HSM) is a well-known compound which is itself useful as a food flavoring substance and as an intermediate in the preparation of polymers and copolymers useful in coatings, electronic applications, ion exchange resins, photoresists, etc.

Although there are several known ways to prepare 4-hydroxystyrene, these known methods are not commercially feasible in the further utilization of the 4-hydroxystyrene. The 4-hydroxystyrene itself is difficult to isolate, since it (1) readily decomposes, (2) is toxic via skin absorption, and (3) readily polymerizes and as a result, those skilled in the art have made numerous attempts to find a method of synthesizing 4-hydroxystyrene in a manner which avoids polymerization and provides the 4-hydroxystyrene in a medium which can be utilized to prepare particular derivatives therefrom.

A preparation for 4-hydroxystyrene utilizing 4-acetoxystyrene is reported in a paper entitled "Preparation of Vinyl-phenols and Isopropylphenols", Corson et al., Volume 23, April 1958 *J. Org. Chem*. In this preparation, 4-acetoxystyrene is saponified in an aqueous system with a large concentration of a base, KOH, to produce an aqueous solution of the potassium salt of 4-hydroxystyrene which is neutralized with acid to precipitate 4-hydroxystyrene, As indicated above, the procedure is not practical or commercially feasible for production of large quantities of 4-hydroxystyrene because the 4-acetoxystyrene and/or the 4-hydroxystyrene is not very stable and readily polymerizes under the aqueous saponification conditions employed therein, which involve high concentrations of soluble base, resulting in poor yields of 4-hydroxystyrene. Thus, a more efficient process for producing 4-hydroxystyrene is desired and needed.

The following prior art references are disclosed in accordance with the terms of 37 CFR 1.56, 1.97 and 1.93.

U.S. 5,087,772 (issued February 11, 1992) discloses the preparation of HSM by reacting 4-acetoxystyrene (ASM) with a suitable alcohol in the presence of a catalytic amount of a suitable base.

European Patent Application 0-128-984 (publication number) filed Aug. 30, 1983 discloses a process for the production of para-vinyl phenol (HSM) by dehydrogenation of para-ethyl phenol.

European Patent Application 0-108-624 (publication number) filed Nov. 4, 1983 discloses a process for the production of p-vinyl phenol polymer (polyhydroxystyrene polymer—PHS) by polymerizing p-vinyl phenol (HSM) in the presence of water and iron.

U.S. Pat. No. 4,032,513 (issued Jun. 28, 1977) discloses a process of producing PHS by cationically polymerizing HSM in the presence of a nitrile, such as $CH_3CN$, using a cationic polymerization initiator in a homogeneous reaction system.

All of the above cited prior art and any other references mentioned herein are incorporated herein by reference in their entirety.

Additional Background Information

This patent application is assigned to the same assignee of that pending patent application Ser. No. 08/029,200 filed Mar. 10, 1993 and entitled "Process for the preparation of p-α-aminoethylphenol" (AEP) and which is incorporated herein by reference in its entirety.

SUMMARY OF THE INVENTION

The present invention provides a unique and novel way of producing vinyl phenols such as p-vinyl phenol (4-hydroxystyrene—HSM). In this new process, p-α-aminoethylphenol (AEP) is heated under suitable deamination conditions of temperature and pressure and for a sufficient period of time to form the 4-hydroxystyrene (HSM).

DETAILED DESCRIPTION OF THE INVENTION

It has unexpectedly been found that HSM can be prepared by heating AEP, with or without a diluent or solvent, for a sufficient period of time under suitable deamination conditions.

The process of the present invention is carried out at a reaction temperature of at least 50° C., preferably between 80° C. and 200° C., and more preferably between 80° C. and 100° C. The reaction pressure may be subatmospheric, atmospheric or superatmospheric. Atmospheric pressure is generally preferred.

The length of time which this heating step is conducted is not critical and the only requirement is that the heating be conducted for a period sufficient to form HSM. Generally, this period is at least five minutes and may be as long as five hours.

Diluents/Solvents which can be used in the present invention include: (a) water; (b) hydrocarbons such as benzene, toluene, xylene and low-boiling point petroleum fractions; (c) inorganic gases such as carbon monoxide, carbon dioxide, nitrogen, helium and argon; (d) dipolaf aprotic solvents; and (e) mixtures thereof. The dipolar aprotic solvents employed are solvents which have a high dielectric constant and a high dipole moment but no acid hydrogen atoms; for example, such solvents include dimethylsulfoxide (DMSO), acetonitrile, dimethylformamide (DMF), dimethylacetamide, hexamethylphosphoric acid triamide (HMPT), and n-methyl pyrrolidone (NMP). Water, benzene, and toluene are preferred diluents. The diluents are used in an amount of 2 to 200 mols, preferably 3 to 20 mols, per mol of AEP. It is to be understood that any diluent may be used under any temperature and reaction conditions so long as the deamination of AEP is effected smoothly.

After the deamination of AEP, the end product HSM is recovered from the reaction product and the residual fraction containing any unreacted AEP can be recycled as the starting material for the next cycle of deamination. The end product HSM may be recovered from the reaction product by any method. One example is to recover the HSM as a polymerized product, i.e., the reaction product is first subjected to a polymerization step to polymerize the HSM and the resulting polymer—polyhydroxystyrene (PHS) is separated from the fraction containing the unreacted AEP by distillation or any other suitable technique.

The following specific example is supplied for the purpose of better illustrating the invention. This example is not intended, however, to limit or restrict the scope of the invention in any way and should not be construed as providing conditions, parameters, or values which must be utilized exclusively in order to practice the present invention.

EXAMPLE 1

Into a one liter flasks equipped with a reflux condenser was charged a mixture of AEP (11.89 grams/0.087 moles) and toluene (50 milliliters). External heating was supplied and the resultant mixture was refluxed (at about 115° C.) for about 45 minutes. During this time substantial quantities of ammonia were given off. GC analysis shaved the presence of HSM.

While the above has been described using p-α-aminoethylphenol (AEP) as the starting material, it is also within the scope of the present invention to use (1) other aminoethylphenols (wherein the aminoethyl and the hydroxy substituents are positioned at different locations on the phenyl ring), and (2) substituted aminoethylphenols wherein the remaining four hydrogen atoms are selectively replaced by an R group, said R being selected from the group consisting of (a) $C_1$–$C_8$ alkyl; (b) $C_6H_5$; (c) halogen (F, Cl, Br, I); (d) hydroxy; and (e) OR where R is the same as defined above. These aminoethylphenols and substituted aminoethylphenols are all suitable starting materials for use in the present invention process.

Although the invention has been illustrated by the preceding example, it is not to be construed as being limited thereby; but rather, the invention encompasses the generic area as hereinbefore disclosed. Various modifications and embodiments can be made without departing from the spirit and scope thereof.

What is claimed is:

1. A process for preparing 4-hydroxystyrene which comprises the step of heating p-α-aminoethylphenol under suitable deamination conditions of temperature and pressure and for a sufficient period of time to form said 4-hydroxystyrene.

2. The process as set forth in claim 1 wherein the temperature is at least about 50° C.

3. The process as set forth in claim 1 wherein the reaction takes place in the presence of an organic solvent.

4. The process as set forth in claim 1 wherein the reaction takes place in the presence of water.

5. The process as set forth in claim 1 wherein the temperature is from about 80° C. to about 100° C.

6. A process for preparing a hydroxystyrene which comprises the step of heating an aminoethylphenol under suitable deamination conditions of temperature and pressure and for a sufficient period of time to form said hydroxystyrene.

7. A process for preparing a hydroxystyrene which comprises the step of heating a substituted aminoethylphenol under suitable deamination conditions of temperature and pressure and for a sufficient period of time to form said hydroxystyrene.

8. The process as set forth in claim 6 wherein the temperature is less than about 100° C. and the heating step is conducted in the presence of an aprotic polar solvent.

9. The process as set forth in claim 7 wherein the temperature is less than about 100° C.; the heating step is conducted in the presence of an aprotic polar solvent; and the formed hydroxystyrene is 3-methyl,4-hydroxystyrene.

* * * * *